United States Patent
Mola et al.

(10) Patent No.: US 10,988,611 B2
(45) Date of Patent: *Apr. 27, 2021

(54) CROSSLINKED POLYVINYLPYRROLIDONE COMPOSITIONS

(71) Applicant: ISP INVESTMENTS LLC, Wilmington, DE (US)

(72) Inventors: Andrew Mola, Highland Lakes, NJ (US); Mustafa Rehmanji, Riverdale, NJ (US); Mika Unting Jan, Cologne (DE)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,546

(22) Filed: Feb. 27, 2018

(65) Prior Publication Data

US 2018/0186995 A1  Jul. 5, 2018

Related U.S. Application Data

(62) Division of application No. 13/132,022, filed as application No. PCT/US2009/066359 on Dec. 2, 2009, now Pat. No. 9,914,829.

(60) Provisional application No. 61/119,463, filed on Dec. 3, 2008.

(51) Int. Cl.
*C08L 39/06* (2006.01)
*C12H 1/056* (2006.01)
*C08J 3/12* (2006.01)

(52) U.S. Cl.
CPC .............. *C08L 39/06* (2013.01); *C08J 3/12* (2013.01); *C12H 1/0424* (2013.01); *C08J 2339/06* (2013.01); *C08L 2312/00* (2013.01)

(58) Field of Classification Search
CPC ..... C08J 2339/06; C08J 3/12; C08L 2312/00; C08L 39/06; C12H 1/0424
USPC ......................................................... 504/361
See application file for complete search history.

(56) References Cited

U.S. PATENT DOCUMENTS

| | | | |
|---|---|---|---|
| 5,484,620 A * | 1/1996 | Oechsle | B01J 20/22 210/670 |
| 6,620,452 B1 | 9/2003 | Haddad et al. | |
| 2003/0032574 A1 | 2/2003 | Meffert et al. | |
| 2004/0043119 A1 * | 3/2004 | Rehmanji | C12H 1/0408 426/422 |
| 2004/0094486 A1 * | 5/2004 | Drohmann | B01D 39/04 210/777 |
| 2004/0107753 A1 | 6/2004 | Narayanan et al. | |
| 2006/0223738 A1 | 10/2006 | Holderbaum et al. | |

* cited by examiner

*Primary Examiner* — Johann R Richter
*Assistant Examiner* — Courtney A Brown
(74) *Attorney, Agent, or Firm* — William J. Davis; Nathalie Tietcheu

(57) ABSTRACT

Low-dusting, granular compositions are provided that comprise at least 15% by weight crosslinked polyvinylpyrrolidone.

5 Claims, 17 Drawing Sheets

CROSSLINKED POLYVINYLPYRROLIDONE COMPOSITIONS

CROSS-REFERENCE

This application is a divisional of U.S. application Ser. No. 13/132,022 filed on Jul. 28, 2011, now allowed (granted as U.S. Pat. No. 9,914,429) which was a national stage of PCT Application No. PCT/US2009/066359 filed Dec. 2, 2009 which claims priority of the provisional application No. 61/119,463 filed Dec. 3, 2008, each of which are hereby incorporated by reference herein in their entirety

FIELD OF THE INVENTION

The invention relates to low-dusting, crosslinked polyvinylpyrrolidone compositions, methods to produce them, and their uses, especially in beverage treatment.

DESCRIPTION OF PRIOR ART

Crosslinked polyvinylpyrrolidone (PVPP), known by the generic chemical name crospovidone in pharma applications, is a water-insoluble, water-swellable, hydrophilic polymer that finds application in multiple industries. It is used in the beverage industries as a drink clarifier and stabilizer, where it binds polyphenols that may lead to astringent flavors anchor hazing (clouding). The complexations through hydrogen bonding and/or dipolar interactions also enable PVPP to serve as a dye scavenger for printing and laundry applications. Finally, due to its compressibility and swelling capacity, crospovidone is widely used in pharmaceutical/nutritional products as a tablet disintegrant.

Commercial PVPP products is sold into commercial sale by a number of manufacturers/suppliers. Polyplasdone® and Polyclar® grades are available from International Specialty Products (Wayne, N.J.). Three grades comprise the Polyplasdone® product line: INF-10, XL, and XL-10. Seven products comprise the Polyclar® product line: Polyclar® 10, Brewbrite™, Plus 730, Super R, Ultra K-100, V, and VT. The Polyclar® Brewbrite™ is a physical blend of PVPP and carrageenan that is effective as a wort clarifier and beer stabilizer. Polyclar® Plus 730 is a beer stabilizer and clarifier consisting of physically blended PVPP and silica xerogel. It is described in U.S. Pat. No. 7,153,534 and is incorporated herein its entirety by reference.

Additionally, the following marketing brochures of International Specialty Products describe these PVPP products used in beverage applications, and hereby are incorporated in their entirety by reference: "Functional drink, tea, and juice stabilizers, clarifiers and texturizers," "Polyclar® 10, Single-use PVPP beer stabilizer," "Polyclar® Brewbrite™, Wort clarifier & beer stabilizer," "Polyclar® Plus 730, Single-use balanced beer stabilizer," "Polyclar® Plus, Prescription clarification and stabilization of beer," "Polyclar® Ultra K-100, Wine stabilizer & clarifier," "Polyclar® for wine," "Polyclar® for beer," "Polyclar® stabilizers for beer," and "Polyclar® stabilizers for wine," Polyclar® Brewbrite™ also is described in an article by Rehmanji, ei al. (2002), which also is incorporated in its entirety by reference.

PVPP is offered for sale by BASF Corp, (Ludwigshafen, Del.) in the Kollidon® CL and Luvicross® product lines. Four grades of pharmaceutical-grade crospovidone compose the Koilidon® CL line: CL, CL-M, CL-F, and CL-SF. The industrial grade of PVPP is sold under the Luvicross® name.

In addition, PVPP of the Sunvidone® CL series is sold by Hangzhou Sunflower Technology Development Co. (Hangzhou, Conn.). Three grades are available, CL-10, CL-30, and CL-100.

In commercial applications, PVPP dust can be problematic as containers (e.g., bags, drums) are emptied and the product filled into hoppers, bins, and used in process equipment. PVPP dust can be collect in these areas where it may manifest itself as cohesive, fine particles that can be difficult to handle and/or settle onto non-target surfaces, unlike the majority of the PVPP product that flows like a granular solid. Such behavior is related to the PVPP particle size distribution. This nuisance may be encountered by smaller-sized companies lacking sophisticated and potentially expensive materials handling equipment.

Such PVPP of small particle size may represent a material loss for the customer. It may be disposed as waste, and may contribute to housekeeping problems. Hence, there is the need for PVPP products that minimize these material handling issues while maintaining product performance without the need for special handling equipment.

In the beer industry where PVPP is valued as a polyphenol absorber, product performance is directly related to particle size. The work of McMurrough et al. (*J Agricult Food Chem*, 43, 10, 2687-2691, 1995) showed, "the adsorptive capacity of commercial PVPP increased with decreasing particle size."

Related to beer stabilization and purification is U.S. Pat. No. 4,820,420, which teaches a centrifugal method for removing polyphenols and/or proteins. The disclosure includes a process in which "kieselguhr, perlite, cellulose, and synthetic fibers or granulated cellulose or synthetic materials arc used as filter means." However, there is no disclosure for a granulated composition containing 15% or more PVPP.

U.S. Pat. No. 4,695,397 teaches a granular bleaching activator that comprises PVPP. This bleaching activator contains from 2.5 parts to 15 parts of a water-swellable assistant, which may be PVPP. U.S. Pat. No. 4,840,799 discloses a process for preparing a rapidly disintegrating, pharmaceutical core wherein a granulate is formed that may comprise PVPP in an amount of 2%-5% (w/w). Again, neither patent discloses a granulated compositions having 15% or more PVPP.

Turning to laundry applications, U.S. Pat. No. 6,900,165 discloses compact, particulate laundry detergents comprising PVPP of a specific particle size distribution. In the compressed laundry tablet, PVPP is present between about 0.5%-20% of the overall mass of the detergent/cleaning product. The aforementioned particle size distribution is as follows:

not more than 10% (w/w) of the PVPP particles have a size less than 63 µm, not more than 30% (w/w) and at least 0.1% (w/w) of the PVPP particle have a size greater than 1000 µm, and at least 10% (w/w) of the PVPP particles have a size less than 200 µm.

Further, the prior art broadly teaches numerous blends having PVPP that are then granulated, including pharmaceutical granulations blended with crospovidone prior to tableting. For example, a rapidly disintegrating tablet comprising a compressed granulate is taught in U.S. Pat. No. 7,282,217. However, a disintegrant, such as crospovidone, as added to the granulate prior to tableting. While PVPP dusting may be experienced, the prior art does not provide solutions to this problem.

Despite the wide use of PVPP in the beverage, cleaning, and pharmaceutical sciences arts, no one has addressed the PVPP dusting problem that exists during material handling operations, particularly with solutions that do not sacrifice the binding capacity of this crosslinked polymer. Additionally, no one has recognized potential benefits in related areas when the dusting problem is resolved by the approach embraced by the current invention.

SUMMARY

In a first embodiment of the invention, low-dusting PVPP compositions are provided by compressing a feed comprising PVPP, and then breaking the compressed composition into granules or grains. Particles sized 100 μm and smaller make up less than 10% (w/w) of the granulated PVPP composition immediately following the compression step. In preferred embodiments, particles sized 100 μm and smaller make up less than 5% (w/w) of the granulated PVPP composition. In highly preferred embodiments, particles sized 170 μm and smaller make up less than 10% (w/w) of the granulated PVPP composition.

The PVPP granulated product comprises at least about 15% PVPP, and more preferably comprise about 30% or more PVPP. Highly preferred embodiments of the invention comprise about 70% or more PVPP.

The invention also claims methods for producing the abovementioned granulated PVPP compositions, having the steps: (A) compressing a feedstock comprising PVPP, and, (B) breaking the compressed feedstock into granules, grains or a powder. In an especially preferred embodiment, the compression step is performed by a roller compactor or an extruder. In a separate, especially preferred embodiment, the breaking step is performed by granulating and/or milling operations.

In another embodiment of the invention, granulated PVPP compositions are used in the production and/or treatment of beverages. In especially preferred embodiments, the granulated PVPP compositions are employed to clarify, stabilize, and/or remove polyphenols from beverages like wine, beer, and tea.

In yet another embodiment of the invention, PVPP is admixed with one or more co-ingredient(s) prior to or during the compressing and/or breaking steps described above. By doing so, any number of formulary ingredients can be combined with PVPP in order to enhance material handling and performance compared to PVPP grades that currently exist. These compositions offer the end user the benefits of reduced dusting and easier materials handling and all-in-one product performance when compared to the individual components. Preferred examples of this embodiment include PVPP and cellulose granules. PVPP and bentonite clay granules, and PVPP with cellulose and bentonite clay granules.

DETAILED DESCRIPTION

Figure 1:
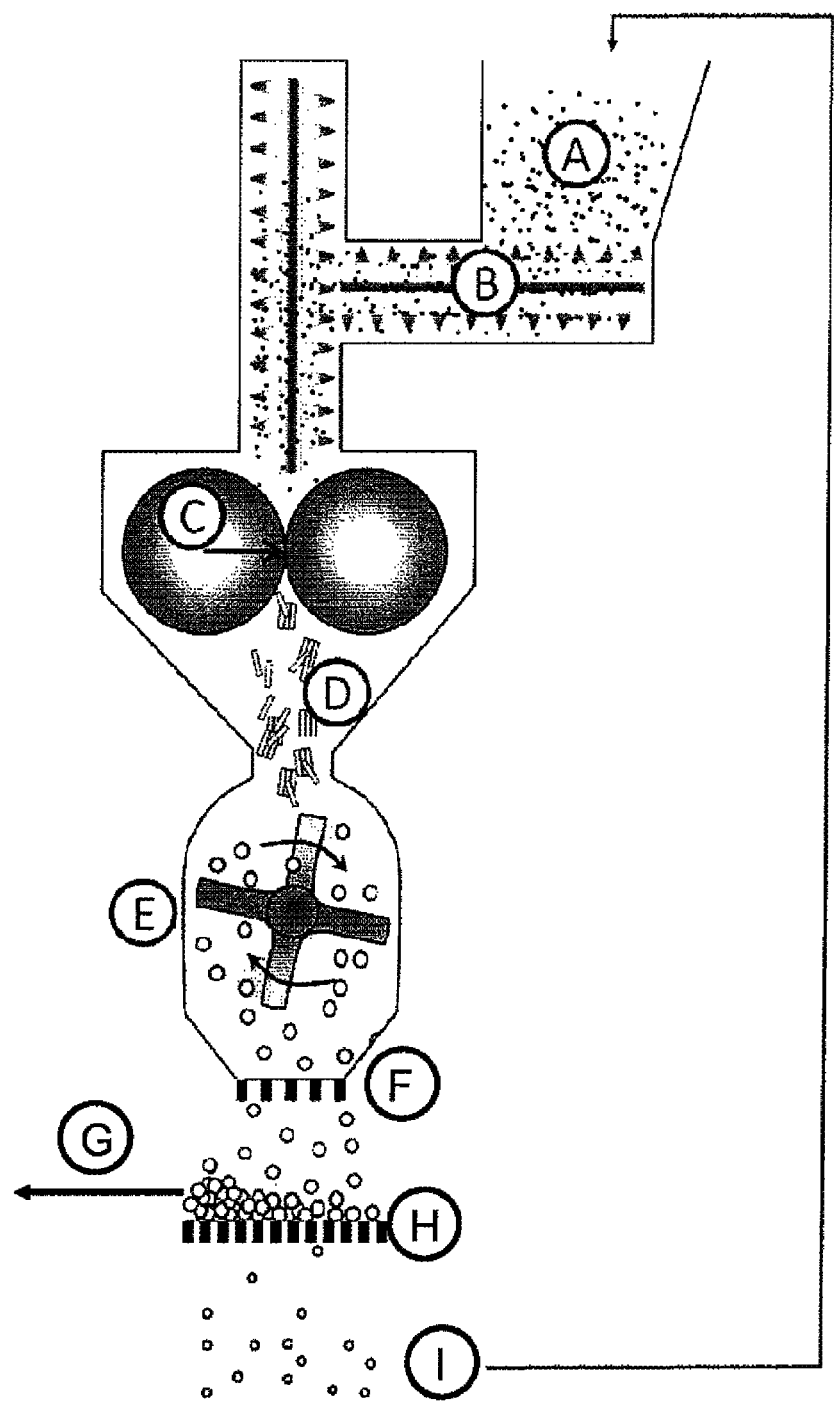
FIG. 1 is a schematic diagram of the process of Example 1.

All percentages, ratio, and proportions used herein are based on a weight basis unless other specified.

Low-dusting PVPP compositions are provided by this invention that resolve the dust problems that are generated from current PVPP grades and products comprising PVPP. A feedstock having PVPP is first compressed and then broken to form granules, grains, or particles. A substantially dust-free product can be produced by returning to the feedstock a fraction of the product that is undersize for re-compression processing. Thus, the low dusting PVPP compositions of nearly any particle size target can be made and then used without special material handling equipment.

When used in beverage applications, it was unexpected that the granulated PVPP products can be substantially free of PVPP dust and yet maintain the original polyphenol absorptive capacity of the unprocessed PVPP feedstock.

In a first embodiment, the feedstock and granulated product consist entirely of PVPP. This low-dusting product can be used alone or in combination with other products in a variety of application arts. For example, the granules may be added to columns used to remove polyphenols during the manufacture of beverages, especially beverages that are made from various grains (e.g., wheat, barley, rice), fruits (e.g., grapes), tea (e.g., green tea), or blends thereof. These beverages typically contain polyphenols and/or proteins, the removal of which may improve the aesthetic or sensory characteristics of the beverage. These beverages may be alcoholic, like vine and beer, or non-alcoholic, like fruit juices and teas.

In a second embodiment, the feedstock comprises PVPP blended with co-ingredients that are selected in order to impart new functionality into the product. Such co-ingredients may convey benefits such as increased and/or new absorptive capacity, compressibility improvement, controlled particle size distribution, and/or enhanced disintegration of subsequent compacted products. For example, co-ingredients like cellulose fiber and/or bentonite clay may be blended with PVPP, co-compressed, and then broken into granules for use in wine making. Nut only are these granules low-dusting, but they also offer convenience to the wine maker for removing polyphenols and proteins in a single processing aide. As shown in the Examples section, the granulated compositions retain 80% or more of the original polyphenol removal of the ungranulated feedstock. Exemplary PVPP granules of the invention retain about 90% or more, or even about 95% or more of the ungranulated polyphenol absorptivity.

It was briefly mentioned earlier that the PVPP-containing compositions are produced from a first compression step performed using methods that are known and/or commercially available. This step aims to consolidate essentially all the feedstock particles into a coherent mass. Also, undersize product can be returned to this step for recompression, which significantly aides in achieving low-dusting product.

Methods capable of performing this compression step include (without limitation): roller compaction, extrusion, and slugging. Roller compactors operate with rotating rolls forming a nip into which the feed is introduced. Feed rate, roll cover material, surface temperature, speed, and compression force are selected per final product requirements. Comixtercially-available roller compactor equipment include: TFC roll compaction systems from Vector Corporation (Marion, Iowa), the WP series roller compactor and granulator line of Alexanderwerk, Inc. (Horsham Pa.), and RC model roller compactors from Powtec Maschinen and Engineering GmbH (Remscheid, Germany).

Extrusion also may be employed in which feed is compacted and forced through a die either at or near room temperature ("cold extrusion") or at elevated temperature ("hot extrusion"). Direct and indirect extruders are known in the art, and include models by Advanced Extruder Technologies (Elk Grove Village, and Wayne Machine & Die Company (Totowa, N.J.).

Slugging is a generic term for compressing materials, typically using dies as in a press such as a tablet or hydraulic press. Examples of a suitable hydraulic presses include the series of presses by Carver, Inc. (Wabash, Ind.).

In addition to this first compression step, a second step is provided for breaking the compressed composition into discrete pieces, such as granules, grains, and powders ("breaking step"). In a preferred embodiment, this second step is performed by a granulator or a mill. Such equipment is commercially available from numerous companies, including: granulators by Sterling (New Berlin, Wis.), granulators by Rapid Granulator, Inc. (Rockford, Ill.), hammer mills and size reduction equipment by Williams Crusher, Inc. (St. Louis, Mo.), and mills from Stedman Machine Co, (Aurora, Ind.).

The granules, grains, and/or powders produced after this breaking step exhibit reduced dusting compared to the starting feed. Within the context of "reduced dusting," particles 100 μm or smaller make up 10% (w/w) or less of the granulated product, more preferably particles 100 μm or smaller make up 5% (w/w) or less of the granulated product, and in especially preferred embodiments, particles 170 μm or smaller make up less than 10% of the product. The mean particle size and particle size distribution conforming to the "reduced dusting" description can be attained by controlling factors related to the first and second steps. For example, prior to the compression step the feedstock can be formulated to affect its compression and friability. The compression step can be regulated with respect to pre-compression force (if any), pre-compression dwell time (if any), compression force, and compression dwell time. Similarly, parameters related to the breaking step can be chosen to control the final product particle size and particle size distribution. If a granulator is employed to break the compressed feedstock, then parameters like feed rate, blade type, blade speed, and exit screen mesh (size) can be selected to achieve the target granule size specifications. For operational efficiency, it is preferred (but not required) that process operations be optimized so that a majority of the product with the desired particle size and particle size distribution exits the one or more exit screens. However, it is possible to achieve these particle size specifications through judicious choice of the exit screens, discarding or recycling any undersize or oversize fraction.

For economic reasons, it is preferred (but not required) that any undersize or oversize fraction from this step be returned for re-compression. If this in-process recycle step is employed when co-ingredients are added to the PVPP feedstock, then it may be necessary to monitor ingredient ratios in the final product so that the target composition specification is attained.

As mentioned, particles 100 μm and smaller make up 10% (w/w) or less of the granulated composition. However, because the compression and breaking steps can be operated within a wide working range, the product is typically larger than 100 μm, for example, greater than 200 μm, and even greater than 400 μm. It is evident that these larger granules obvious any dusting concern as exhibited by the unprocessed starting material.

Determination of the particle size may be made by methods known in the art, provided that an adequate sample is selected for measurement and properly handled so that represents the product after its productio.

It may be preferred to perform the compression and breaking steps using one piece of process equipment. Equipment to provide benefits in time, material handling, product quality, and product yield are known, and include the Chilsonator® by the Fitzpatrick Co. (Elmhurst, Ill.).

Depending on the types of process equipment, their operation, and the desired reduction in product dust, it may be advantageous to size fractionate material exiting the breaking process step and return to the feedstock an undersized fraction for additional compression processing. Such size fractionation may be accomplished using known methods, such as screening using sieve(s) of a desired mesh.

It has been surprisingly discovered that additional co-ingredients can be added to the feedstock to produce not only a low-dust product, but products of increased functionality. The methods and compositions of the invention are utile when the co-ingredient(s) exhibit dusting tendencies, especially if the particle size of the uncompressed co-ingredient is about 100 μm or less. Such products exhibit properties not achieved when PVPP is processed alone. Such additional materials include, without limitation: absorbents, active ingredients, adsorbents, beverage process aides, binders, complexation aides disintegrants, disintegrant aides, lubricants, plasticizers, polyphenol absorbers, protein absorbers, stabilizers, surfactants, wetting agents, and wicking agents.

Absorbents and adsorbents are those materials that absorb substances or cause substances to accumulate on the surface. Absorbents/adsorbents exhibit reversible or permanent complexation interactions with the substance, e.g., through hydrogen bonding and/or dipole interaction, Absorbents and adsorbents are commonly used in the chemical arts as carriers, clarifiers, and purifiers. They are known by beer, fruit juice, and wine manufacturers for their ability to improve beverage taste, color, and shelf life. Examples of absorbents and adsorbents used in the beverage industry include, in addition to PVPP: activated carbon, bentonite clay, carrageenan, diatomaceous earth, polysaccharides, and silica xerogel. Unlike PVPP, which exhibits affinity for polyphenol complexation, these absorbents/adsorbents selectively absorb proteins, and, for example, find extensive use in the manufacture of white wine.

Absorbents/adsorbents also are used in the laundry, ink, and printing arts where they fix a target compound(s) in order to avoid color bleeding, release, and transfer. Examples of complexation aides include co- and terpolymers of dimethylaminopropylmethaerylamide, such as ViviPrint™ 200 and 300; polyvinylpyrrolidone, such as Plasdone® grades (all International Specialty Products); and amorphous silica gel, such as Silcron® IJ-50 (Millennium Chemicals). The utility of co-compressing PVPP with other absorbents/adsorbents is self apparent.

In the beverage industry, kappa-carrageenan, bentonite clay and silicas (e.g., silica xerogel, silica hydrogel, silica aerogel, and silica sol) are complexation aides that are useful for the removal of haze-producing drink constituents. Kappa-carrageenan is a hydrocolloid extract from red seaweed that is very effective at reducing non-microbiological particles (e.g., proteins, polyphenols, and polysaccharides) from wort. Non-biological haze results primarily from the hydrogen bonding between haze-producing; proteins and polyphenol constituents of beer.

Bentonite clay is an aluminosilicate that effectively removes proteins from white wine. It consists principally of montmorillonite with various impurities, such as kaolinite. As an absorbent, bentonite can remove large amount of proteins that otherwise denature and precipitate during wine aging and/or when brought to room temperature.

Silica xerogel is another non-additive absorbent used together with PVPP in the beverage industry. Silica xerogels are free-flowing, non-crystalline (amorphous) silicon dioxide that is also known by the synonym silica gel. Silica xerogels are employed by brewers to remove haze-producing proteins.

In addition to beverage process aides, active ingredients may be included for use in this invention. Active ingredients are defined as those chemical compounds that elicit a response due to their chemical nature. Categories of actives include biocides, fertilizers, fragrances, nutritionals, pharmaceuticals, and reactants. When co-compressed with PVPP to product low-dusting, granular products, active ingredients may exhibit enhanced solubility and/or bioavailability. In preferred embodiments, the active ingredient is a biocide, a fertilizer, a nutritional, or a pharmaceutical active.

Within this context, biocide, refers any composition that kills life by poisoning it, and includes; algaecides, aquaticides, insecticides, fungicides, germicides, herbicides, larvicides, pesticides, rodentcides, and taeniacides. It is noted that both organic and inorganic materials exhibit biocidal activity.

Examples of algaeeides/fungicides/mildeweides include: 3-allyloxy-1,2-benzoisothiazol-1,1-dioxide; basic copper chloride; basic copper sulfate; 1,2-benzisothiazoline-3-one; methyl-N-(1H-benzoimidazol-2-yl) carbamate (carbendazim); 2-(tert-butylamino)-4-(cyclopropylamino)-6-(methylthio)-s-triazine (Irgarol®); 2-tert-butylamino-4-ethylamino-6-methylmercapto-s-triazine (terbutryin); S—N-butyl-5'-para-tert-butylbenzyl-N-3-pyridyldithiocarbonylimidate; 2-chloro-1-(3-ethoxy-4-nitrophenoxy)-4-(trifluromethyl) benzene (oxyfluorfen); 4-chlorophenoxy-3,3-dimethyl-1-(1H,1,3,4-triazol-1-yl)-2-butanone; α-[2-(4-chlorophenylphenyl)ethyl]-α-(1,1-dimethylethyl)-1H-1,2,4-triazole-1-ethanol (tebuconazole); copper 8-quinolinate; cycloheximide; bis-(dimethyldithio-carbamoyl) disulfide; 11-dehydrodibenzo (b,f)azepine; 2,4-dichloro-6-(0-chloroanilino)-1,3,5-triazine; 1,4-dichloro-2,5-dimethoxybenzene; N'-dichlorofluoromethylthio-N,N-dimethyl-N-phenyl sulfamide; 2,3-dichloro-1,4-naphthoquinone; 2,6-dichloro-4-nitroaniline; 4,5-dichloro-2-N-octyl-4-isothiazolin-3-one (DCOIT); N-(3,5-dichlorophenyl)-1,2-dimethylcyclopropane-1,2-dicarboxyimide; N'-(3,4-dichlorophenyl)-N,N-dimethylurea (diuron); 1-[2-(2,4-dichlorophenyl)-4-ethyl-1,3-dioxorane-2-ylmethyl]-1H,1,2,4-triazol; N-(3,5-dichlorophenyl) succinamide; 1-[[2(2,4-dichlorophenyl)-4-propyl-1,3-dioxolan-2-yl]methyl]1-H-1,2,4-triazole (propiconazole); N-2,3-dichlorophenyltetrachlorophthalmic acid; 3-(3,5-dichlorophenyl)5-ethenyl5-methyloxazolizine-2,4-dione; 2,3-dicyano-1,4-dithioanthraquinone; N-(2,6-diethylphenyl)-4-methylphthalimide; N-(2,6-p-diethylphenyl) phthalimide; 5,6-dihydro-2-methyl-1,4-oxathine-3-carboxanilide; 5,6-dihydro-2-methyl-1,4-oxathine-3-carboxanilido-4,4-dioxide; diisopropyl 1,3-dithiolane-2-iridene malonate; O,O-diisopropyl S-benzylphosphorothioate; 2-dimethylamino-4-methyl-5-N-butyl-6-hydroxypyrimidine; bis-(dimethyldithiocarbamoyl) ethylenediamine; 5-ethoxy-3-trichloromethyl-1,2,4-thiaziazole; ethyl-N-(3-dimethylaminopropyl)thiocarbamate hydrochloride; O-ethyl S,S-diphenyldithiophosphate; 3,3'-ethylene-bis-(tetrahydro-4,6-dimethyl-2H-1,3,5-thiadiazine-2-thione); 3-hydroxy-5-methylisoaxazole; 3-iodo-2-propargyl butyl carbamate (IPBC); irgarol, iron methanearsonate; 3'-isopropoxy-2-methylbenzanilide; 1-isopropylcarbamoyl-3-(3,5-dichlorophenyl) hydantoin; kasugamycin; manganese ethylene-bis-(dithiocarbamate); 1,2-bis-(3-methoxycarbonyl-2-thioureido) benzene; methyl-1(butylcarbamoyl)-2-benzimidazolecarbamate; 5methyl-10-butoxycarbonylamino-10; 3-methyl-4-chlorobenzthiazol-2-one; methyl-D,L-N-(2,6-dimethylphenyl)-N-(2'-methoxyacetyl)alaninate; S,S-6-methylquinoxaline-2,3-diyldithiocarbonate 5-methyl-s-tri azol-(3,4-b)benzthiazole; nickel dimethyldithiocarbamate; 2-octyl-2H-isothiazol-3-one (OIT); 2-oxy-3-chloro-1,4-naphthoquinone copper sulfate; pentachloronitrobenzene; (3-phenoxyphenyl)methyl (+/−)-cis,trans-3-(2,2-dichloroethenyl)-2,2-dimethylcyclopropanecarboxyate (permethrin); piomycin; polyoxine; potassium N-hydroxymethyl-N-methyldithiocarbamate; N-propyl-N-[2-(2,4,6-trichlorophenoxy)ethyl]imidazol-1-carboxamide; 2-pyridinethiol-1-oxide sodium salt; sodium pyrithione; N-tetrachloroethylthio-4-cyclohexene-1,2-dicarboxylmide; tetraohloroisophthalonitrile; 4,5,6,7-tetrachlorophthalide; tetrahydro-4H-1-pyrrolo-[3,2,1-i,j]quinoline-2-one; 2-(thiocyanomethyithio)benzothiazole; N-trichloromethylthio 4-cyclohexene-1,2-dicarboxyimide; N-(trichloromethylthio)phthalimide; validamycin; zinc ethylene-bis-(dithiocarbamate); zinc bis-(1-hydroxy-2(1H) pyridinethionate; zinc propylene-bis-(dithiocarbamate); and zinc pyrithione.

Commercial examples of biocides include (in alphabetical order): amine reaction products (Nuosept® 145), 1,2-benzisothiazolin-3-one (Nuosept® 495, 497, 498), 2-bromo-2-nitropropane-1,3-diol (bronopol) (Nuosept® 330), 3-iodo-2-propargyl butyl carbamate (IPBC) (Fungitrol® 440S, 400SE, 420S, 430S, 440S, 720, 920, 930, 940), 5-chloro-2-methyl-4-isothiazolin-3-one (CMIT)/2-methyl-4-isothiazoli-3-one (MIT) (Nuosept® 515R), bicyclic oxazolidines (Nuosept® 95), glutaraldehyde (Nuosept® 210), N-(trichloromethylthio)phthalimide biocides (folpet) (Fungitrol® 11 and 11-50S, PlastiGuard® 11PE), tetrachloroisophthalo-nitrile biocides (Fungitrol 404-D and 960), tetrahydro-3,5- dimethyl-2h-1,3,5-thiodiazine-2-thione (Nuosept® S), all offered for sale by international Specialty Products (Wayne, N.J.).

A plant growth regulators are a chemical compound that alters the growth and/or the productivity of plants, and comprise herbicides and fertilizers. Plant growth regulators include inorganic and organic fertilizers, and contain micro- and macronutrients such as ammonia, urea, ammonium nitrate, ammonium sulfate, and compounds containing magnesium, nitrogen, phosphorus, and potassium. Examples of plant growth regulators include: N-methexycaronyl-N'-4-methylphenylcarbamoylethylisourea; 1-(4-chlorophenylcarbamoyl)-3-ethoxycarbonyl-2-methylisourea; sodium naphthaleneacetate; 1,2-dihydropyridazine-3,6-dione; and gibberellins.

Examples of herbicides include (in alphabetical order): 5-bromo-3-sec-butyl-6-methyluracil; 5-tert-butyl-3-(2,4-dichloro-5-isopropoxyphenyl)-1,3,4-oxadiazoline-2-one; S-(4-chlorobenzyl)-N,N-diethylthiolcarbamate; 2-chloro-4,6-bisethylamino-1,3,5-triazine; 2-chloro-2',6'-diethyl-N-(butoxymethyl)acetoanilide; 2-chloro-2',6'-diethyl-N-(methoxymethyl)acetoanilide; 2-chloro-4-ethylamino-6-isopropylamino-s-triazine; 2-chloro-4-methylphenoxyacetic acid; 4-chloro-2-methylphenoxyacetic acid; 3-(4-chlorophenyl)-1,1-dimethyl urea; 1-cyclohexyl-3,5-propyleneuracil; 2,4-dichlorophenoxyacetic acid, and methyl-, ethyl-, and butyl-esters thereof; 3-(3,4-dichlorophenyl)-1,1-dimethylurea; 3-(3,4-dichlorophenyl)-1-methoxy-1-methyl urea; 2,4-dichlorophenyl-4'-nitrophenylether; 3,4-dichloropropioneanilide; N[3],N[3]-diethyl-2,4-dinitro-6trifluoromethyl-1,3-phenylene diamine; 1,1'-di-methyl-4,4'-bis-pyridinium dichloride; 1,3-dimethyl-4-(2,4-dichlorobenzoyl)-5-hydroxypyrazole; 1,3-dimethyl-4-(2,4-dichlorobenzoyl)-5-(p-toluenesulfonyloxy)pyrazole; 3,5-dimethylphenyl-4'-nitrophenylether; diphenylether ethyl 2-methyl-4-chlorophenoxybutylate; S-ethyl-N-cyclohexyl-N-ethylthioicarbamate; S-ethyl-hexahydro-1H-azepine-1-carbothioate; S-ethyl-N,N-di-N-propyl-thiocarbamate; 3-isopropylbenzo-2-thia-1,3-diazinone-(4)-2,4-dioxide; 2-[N-isopropyl,N-(4-chlorophenyl)carbamoyl]-4-chloro-5-methyl-4-isooxazoline-3-one; isopropyl-N-(3-chlorophenyl)carbamate; 3-methoxycarbonylaminophenyl-N-(3-methylphenyl)carbamate; 2-methoxy-4-ethylamino-6-isopropylamino-1,3,5-triazine; methyl-N-(3,4'-dichlorophenyl)carbamate; 3-(2-methyl-pherioxy) pyridazine 4-(methylsulfonyl)-2,6-dinitro-N,N-dipropylaniline; 2-methylthio-4,6-bis-ethylamino-1,3,5-triazine; 2-methylithio-4-ethylamino-6-isopropylamino-s-triazine; 2-methylthio-4,6-bis-(isopropylamino)-S-triazine; N-(phosphonomethyl)glycine; 2,4,6-trichlorophenyl-4'-nitrophenylether; and α,α,α-trifluoro-2,6-dinitro-N,N-dipropyl-p-toluidine.

Binder are chemical compositions that cause components of a mixture to stick (or bind) together, and may be included for compression with PVPP in the feedstock. It is envisioned that binders may find special application for granulated compositions comprising PVPP; binders help create a consolidated mass after compression, especially when poorly compressible co-ingredients are added to feedstock comprising PVPP. Many binders are known in the prior art, and are limited only inasmuch as they be suitable for the final product, the intended application, and product attributes. Specific examples of binders include, without limitation (in alphabetical order): acacia, celluloses, lactoses, oils, polyols, polysaccharides, polyvinylpyrrolidones, starches, and tragacanth, and their respective derivatives.

Disintegrant aides and wicking agents may be included with PVPP in the feedstock. Disintegrant aides are those materials that assist in the break-up of compressed forms, wherein wicking agents serve to transport liquids, especially water, by virtue of their form and chemical composition. Both disintegrant aides and wicking agents are widely used in compressed and uncompressed product forms, such as tablets and capsules/sachets. Examples of disintegrant aides and wicking agents include: alginic acid, calcium silicate, carboxymethylcellulose sodium, celluloses (e.g., microcrystalline and powdered), chitosan, colloidal silicon dioxide, croscarmellose sodium, guar gum, hydroxypropylcellulose, magnesium aluminum silicate, methylcellulose, polacrilin potassium, sodium alginate, sodium bicarbonate, sodium starch glycolate, and starch. Pharmaceutically-approved disintegrant aides and wicking agents are described in *The Handbook of Pharmaceutical Excipients* by R. C. Rowe P. I. Sheskey, and S. C. Owen (Pharmaceutical Press and American Pharmaceutical Association, 2003), which is incorporated in its entirety by reference.

It is envisioned that the feedstock comprising PVPP may be directly compressed "as is." Yet, it is also contemplated that humidification of the feedstock may assist the compression step and yield product further reduced in fines content. Water is a known plasticizer, meaning it lowers the glass transition temperature of non-crystalline materials. Humidification may improve the compressibility of the feedstock, and may prove helpful if the blended co-ingredients require improved compressibility. It is preferred that humidification (if any, of the feedstock be sufficient to promote compressibility without causing processing difficulties such as roll sticking. Furthermore, it is recognized that feedstock humidification may be attained simply by virtue of where the materials are stored, e.g., a warehouse or processing floor of sufficient humidity, especially for hygroscopic and/or hydrophilic feedstock materials (e.g., PVPP).

Additionally, it is contemplated that the feedstock may comprise other plasticizers to enhance the plastic properties of feedstock composition, for example, increasing flexibility and/or durability by lowering the glass transition temperature ($T_g$) of the composition. Other examples of such plasticizers include (in alphabetical order): citrates (e.g., acetyltributyl, acetyltriethyl, tributyl, and triethyl citrates), glycols (e.g., polyethylene glycol and propylene glycol, glycerin), medium-chain triglycerides (e.g., mixtures of caprylic acid and capric acid), phthalates (e.g., dibutyl, diethyl, and dimethyl phthalates), stearates (e.g., glyceryl monostearate), and triacetin. The necessary plasticizer addition level is dependent on the degree of plasticization needed.

Yet other co-ingredients may be included with PVPP in the feedstock for compression processing.

The invention will now be described with particular reference to the following non-limiting examples:

EXAMPLES

Example 1

Two grades of food-grade PVPP, Polyclar® XG and Polyclar® 10 (International Specialty Products), were individually compressed using a TF Mini Roller Compactor (Vector Corporation, Marion, Iowa) operating with a screw speed of about 83 rpm, a roller speed of 6.5 rpm, and a roller pressure of 4 tons.

The resultant ribbons from the roller compactor were granulated using an Erweka® AR400 Oscillating Granulator (Heusenstamm, Germany). The granular solid products were size fractionated using 10 mesh and 18 mesh screens. Product passing through the 18 mesh screen ("fines") was returned to the feed for re-compression processing.

FIG. 1 presents a schematic diagram of the process, wherein

Item A represents the feedstock bin.
Item B represents the auger feeder system.
Item C represents the roller compacter rolls and the nip they form (at arrow).
Item D represents the compressed ribbon exiting the rollers.
Item E represents the granulator.
Item F represents a first screen at the exit of the granulator.
Item G represents granulated product having a size smaller than the mesh of screen F, but larger than the mesh of screen H.
Item H represents a second screen, finer than screen F, for fines removal.
Item I represents undersize product that passed through the second screen (Item H) that is redirected back to the feedstock bin for additional compression processing.

Figure 2:
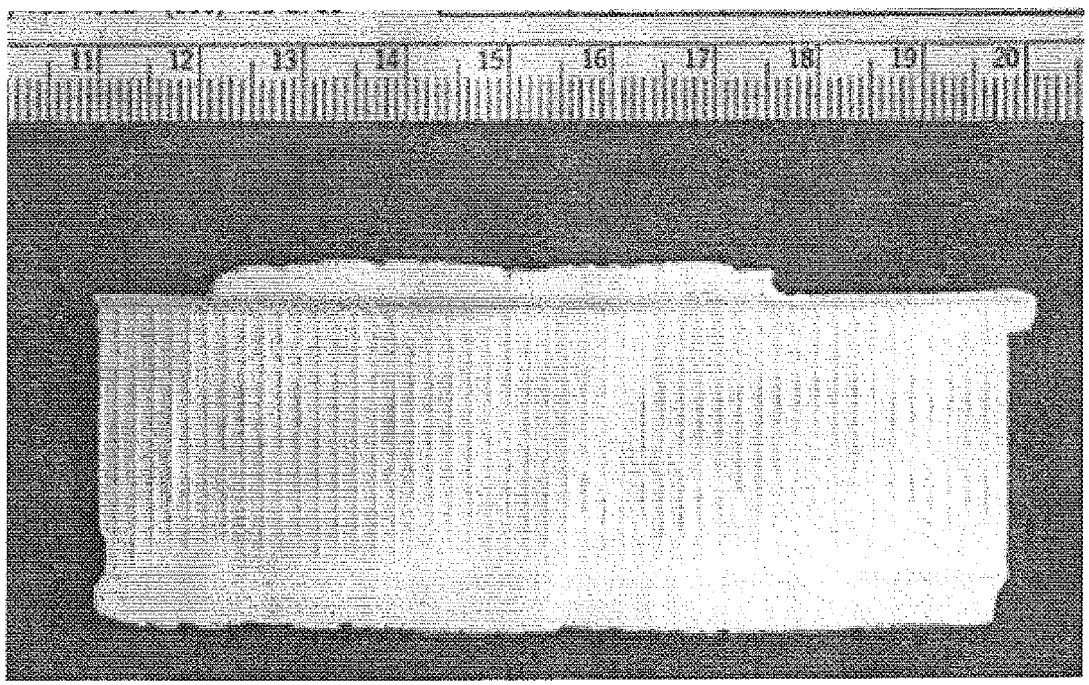
FIG. 2 is a photograph of a composition produced in accordance with Example 1.

A photograph of a compressed PVPP ribbon is shown in FIG. 2.

Figure 3:
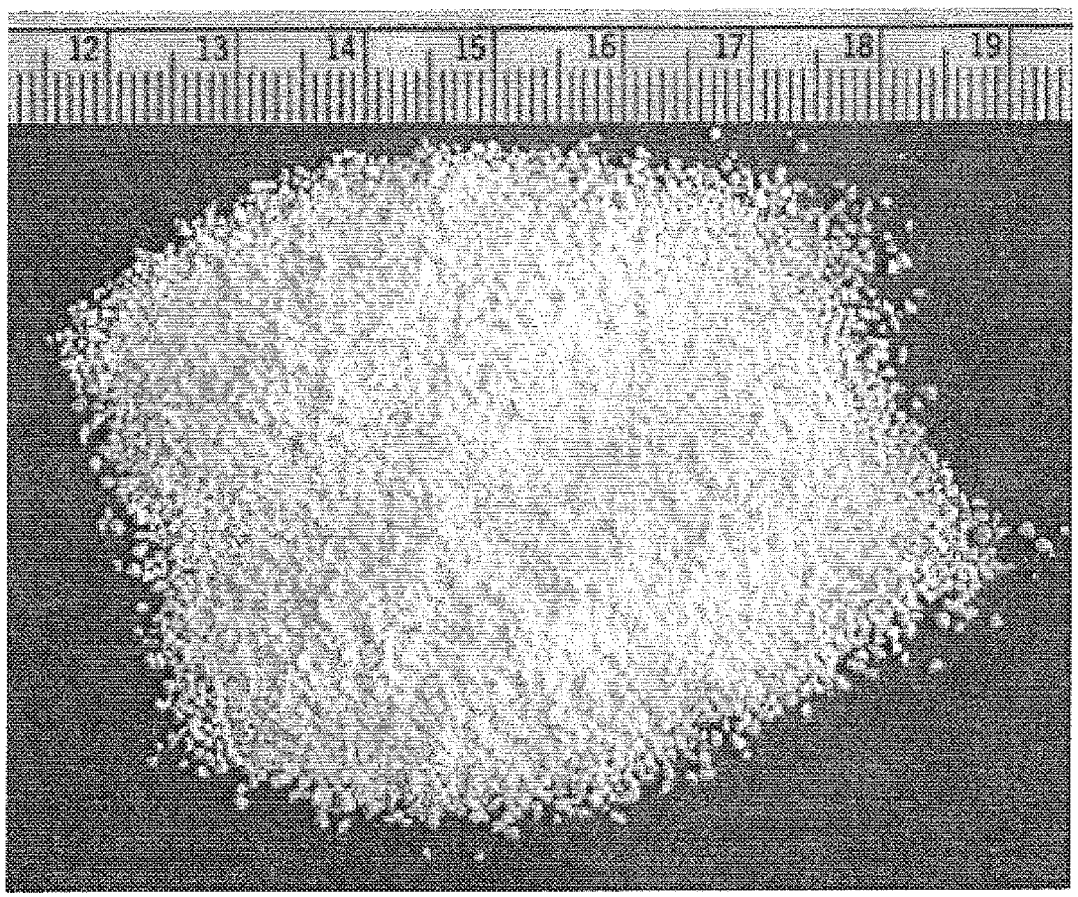
FIG. 3 is a photograph of a composition produced in accordance with Example 1.
Figure 4:
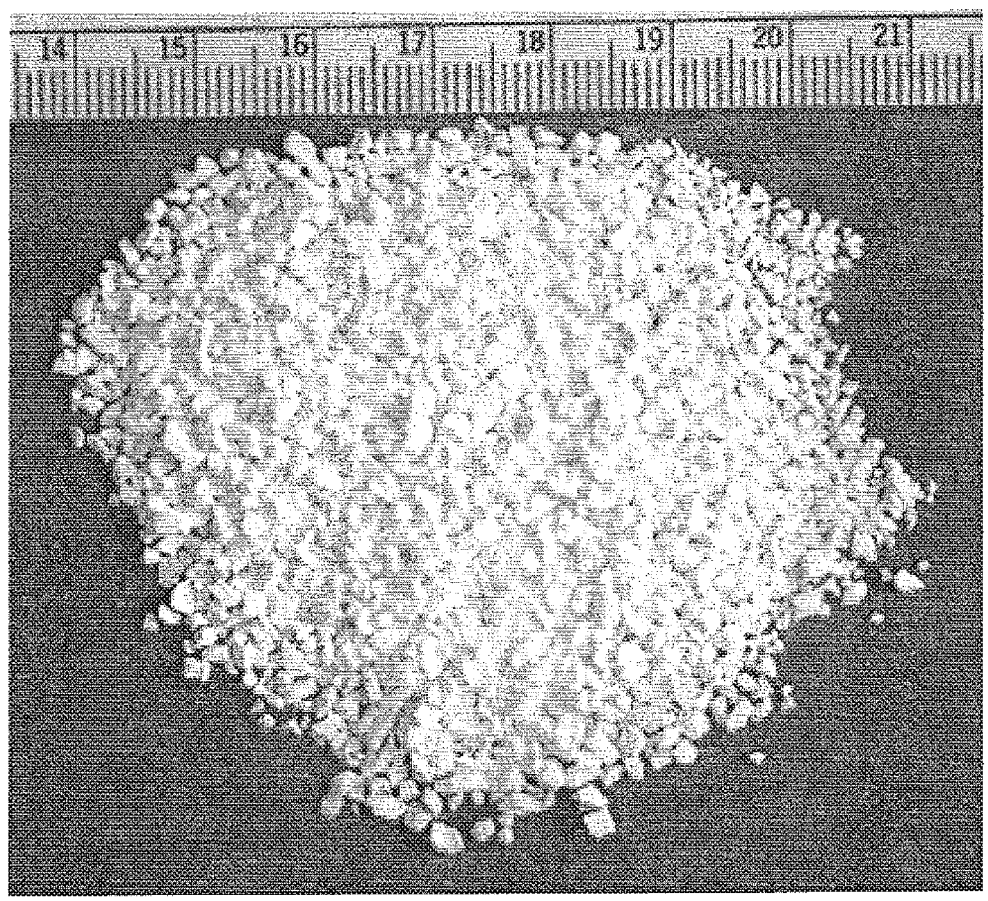
FIG. 4 is a photograph of a composition produced in accordance with Example 1.

Granular, low-dusting PVPP product was produced upon discharge from the granulator. Photographs of the two lots of granular products are illustrated in FIGS. 3 and 4, wherein the shown ruler is a standard metric ruler with 1-mm gradations.

Example 2

The dry and hydrated particle size distributions were measured for the two product lots produced in Example 1. A Malvern Mastersizer S (Malvern Instruments Ltd., Worcestershire, UK) was employed with a range lens of 300 mm, a beam length of 10.00 mm, a particle refractive index of 1.729+i0.1000, a dispersant (air) refractive index of 1.000+i0.000, and 5000 sweeps.

Upon rehydration, the granular products disintegrated to almost the original particle size distribution of the unprocessed feedstock PVPP (table 1).

TABLE 1

Particle size distribution results of Example 2.

| material | state of material | particle size distributions (μm) | | | |
|---|---|---|---|---|---|
| | | $d_{10\%}$ | $d_{50\%}$ | $d_{90\%}$ | span |
| Polyclar ® XG | feedstock powder: unprocessed, dry | 6.1 | 11.5 | 18.2 | 1.0 |
| | feedstock powder: unprocessed, hydrated | 2.9 | 14.3 | 23.8 | 1.5 |
| | compressed + granulated product: 10 mesh, hydrated | 5.0 | 18.2 | 44.4 | 2.2 |
| | compressed + granulated product: 18 mesh, hydrated | 4.5 | 16.6 | 37.8 | 2.0 |
| Polyclar ® 10 | feedstock powder: unprocessed, dry | 12.7 | 23.9 | 42.9 | 1.3 |
| | feedstock powder: unprocessed hydrated | 9.0 | 30.1 | 76.3 | 2.2 |
| | compressed + granulated product: 10 mesh, hydrated | 8.6 | 30.4 | 82.3 | 2.4 |
| | compressed + granulated product: 18 mesh, hydrated | 8.3 | 30.1 | 81.9 | 2.4 |

Method 1: Catechin (a Polyphenol) Absorption Test

Standard Solution: In an amber volumetric flask 80 mg catechin hydrate (+catechin hydrate, Aldrich Chemical Company, Milwaukee, Wis.) was dissolved in 50 mL of ethanol, which was then diluted 1 L with distilled water.

Reference Solution: In a volumetric flask 50 mL ethanol (absolute) was diluted to 1 L with distilled water.

Water content of beverage treatment aide: The water content of the PVPP beverage aide was determined using Kari Fisher analysis.

Test Solutions (in duplicate): A 50 mg sample of beverage treatment aide (weight corrected for moisture content) was weighed and added to a beaker containing a Teflon® magnetic stir bar. To this beaker was added 100 mL of Standard Solution and the sample was stirred by the magnetic stir bar. After exactly 5 minutes of stirring, an aliquot was withdrawn was passed through a 0.45 μm Teflon® filter. The filtered sample was stored in a cool, dark place for a maximum of 1 hour before measuring the UV absorbance.

Blank Solution: A 50 mg sample of beverage treatment aide (weight corrected for moisture content by Karl Fisher analysis) was weighed and added to a beaker containing a Teflon® magnetic stir bar. To this beaker was added 100 mL of Reference Solution and the sample was stirred by the magnetic stir bar. After exactly 5 minutes of stirring, an aliquot was withdrawn was passed through a 0.45 μm Teflon® filter. The filtered sample was stored in a cool, dark place for a maximum of 1 hour before measuring the UV absorbance.

The absorbances were measured for the two filtered Test Solution and the Blank Solution aliquots using 1 cm quartz cuvettes at 280 nm using a Perkin Elmer spectrophotometer, model 559A (Waltham, Mass.). The Reference Solution was used to zero the spectrophotometer, and served as the reference for each filtered sample.

The polyphenol absorption of the beverage treatment aide was calculated as:

$$A = \frac{A_o - (A_\tau - A_b)}{A_o} \times 100$$

wherein:
$A_o$ is the polyphenol absorption of the Standard Solution,
$A_\tau$ is the polyphenol absorption of the Test Solution, and
$A_b$ is the polyphenol absorption of the Blank Solution,
The average of the two Test Solutions was reported for each beverage treatment aide.

Example 3

The adsorptive capacity was measured by Method 1 for the untreated and treated lots of Example 1.

Contrary to expectation, no loss in adsorptive capacity was measured for the granulated, low-dusting PVPP products (Table 2).

TABLE 2

Adsorptive capacity results of Example 3.

| PVPP grade | test material | polyphenol absorption |
|---|---|---|
| Polyclar ® XG | uncompressed feedstock powder | 60.2% |
| | compressed + granulated product: 10 mesh | 59.8% |
| | compressed + granulated product: 18 mesh | 60.8% |
| Polyclar ® 10 | uncompressed feedstock powder | 56.1% |
| | compressed + granulated product: 10 mesh | 55.9% |
| | compressed + granulated product: 18 mesh | 55.1% |

Method 2: Measurement of Haze-Producing Polyphenols and Proteins

The PT Standard automatic titrator made by OPTO-EMS (Darmstadt, Germany) was used to measure the content of haze-producing polyphenols and proteins. This instrument automatically doses a reagent specific to polyphenois (T125, a proprietary reagent based on polyvinylpyrrolidone) or proteins (P40, a proprietary reagent based on ammonium sulfate). These reagents form complexes with polyphenol and "salt out" proteins, respectively, to quantify their content in beverages. In each case the resulting beverage haze initially increases with reagent addition, then decreases. The reported value coincides with the maximum haze of a test sample.

Beer test solution: Granulated beverage treatment aide (e.g., granulated PVPP) was weighed and added to a beaker containing a Teflon® magnetic stir bar.

To the beverage treatment aide was a beer sample, and the sample was stirred by the magnetic stir bar.

After exactly 5 minutes of stirring, an aliquot was withdrawn and was passed through a 0.45 μm filter.

A 4-mL sample of filtered beer was added to a clean PT Standard cuvette, which was placed in the measurement chamber and the dosing head positions.

After a 30-second equilibration, the instrument was zeroed to obtain the reference haze value.

The titration was initiated by clicking, "start" using either the P40 reagent (for protein analysis) or the T125 reagent (for polyphenol analysis).

Automatic titration and haze measurement was performed by the PT Standard instrument to a pre-programmed haze value is attained.

Results are reported in units of "mL reagent/100 mL beer." Increasing values indicate increased reagent demands, and therefore increasing beer stability.

Example 4

Method 2 was applied to measure the absorptive performance for six granulated beverage treatment aides. American-style lager was tested at 10 g PVPP/hL (=100 mg PVPP/L).

No loss in haze stability was measured using the compositions produced in Example 1 (Table 3),

TABLE 3

Haze stability titers of Example 4.

| material | test material | titer value (mL) T-125 reagent (polyphenols) | titer value (mL) P-40 reagent (proteins) |
|---|---|---|---|
| Polyclar ® XG | feedstock powder | 40.8 | 34.8 |
| | compressed + granulated product: 10 mesh | 39.7 | 34.6 |
| | compressed + granulated product: 18 mesh | 39.1 | 35.2 |
| Polyclar ® 10 | feedstock powder | 34.1 | 33.7 |
| | compressed + granulated product: 10 mesh | 32.1 | 34.1 |
| | compressed + granulated product: 18 mesh | 32.7 | 33.4 |
| | untreated beer | 12.4 | 32.6 |

Example 5

Figure 5:
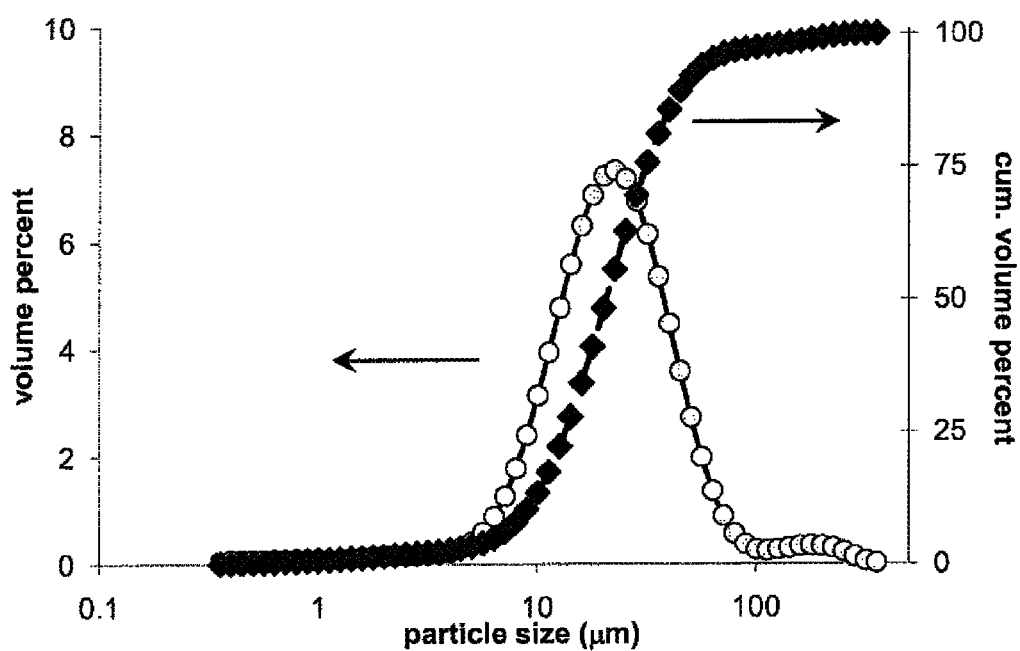
FIG. 5 is a graph describing a particle size distribution of a composition produced in accordance with Example 5.

The particle size distribution of a crosslinked polyvinylpyrrolidone, sold under the trade name Polyclar® 10 (International Specialty Products), was analyzed in the dry state by a light-scattering technique (Malvern Instruments, Malvern, UK). The results indicate that the 50th percentile particle size ($d_{50}$) was about 23 μm (FIG. 5). About 10% of the particles were smaller than 10 μm.

The described lot of Polyclar® 10 was dry roller compacted by a Chilsonator® (Fitzpatrick Company, Elmhurst, Ill.) operating with both horizontal and vertical feed augers. The compaction roller space was adjusted so that a compacted PVPP ribbon was produced.

The compressed ribbon was fed to a hammer mill to granulate the compressed product. Product was discharged from the mill through a 10 mesh screen onto a vibratory screener Fitted with either a 20 mesh or 4:2 screen.

Example 6

The dry, granular product of Example 5 was size fractionated using a Ro-Tap rotary tapping sieve shaker (Laval Lab, Quebec, Calif.) equipped with four screens: 80 mesh (0.178 mm), 40 mesh (0.422 mm), 20 mesh (0,854 mm), and 10 mesh (2.06 mm) screens.

Figure 6:
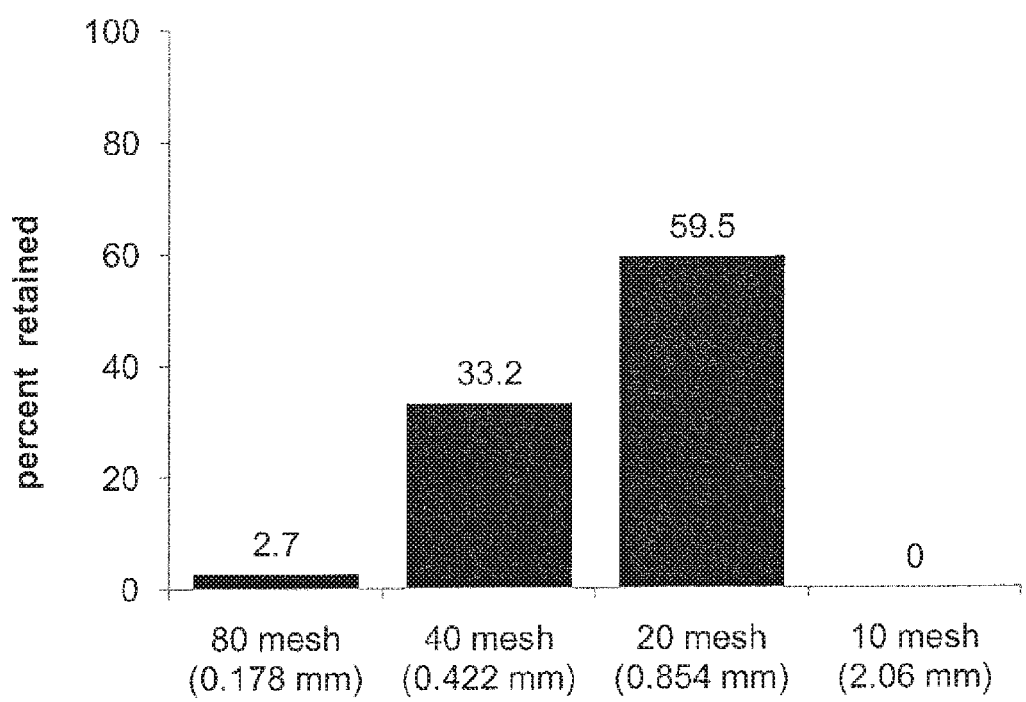
FIG. 6 is a graph describing a particle size distribution of a composition produced in accordance with Example 6.

No granular product was retained on the 10 mesh screen, while more than half of the granular product was collected on the 20 mesh screen (FIG. 6). Particles smaller than 80 mesh (178 μm) made up 4.6% of the product.

Example 7

Three Formulated PVPP Granules for Wine Making

Figure 7:
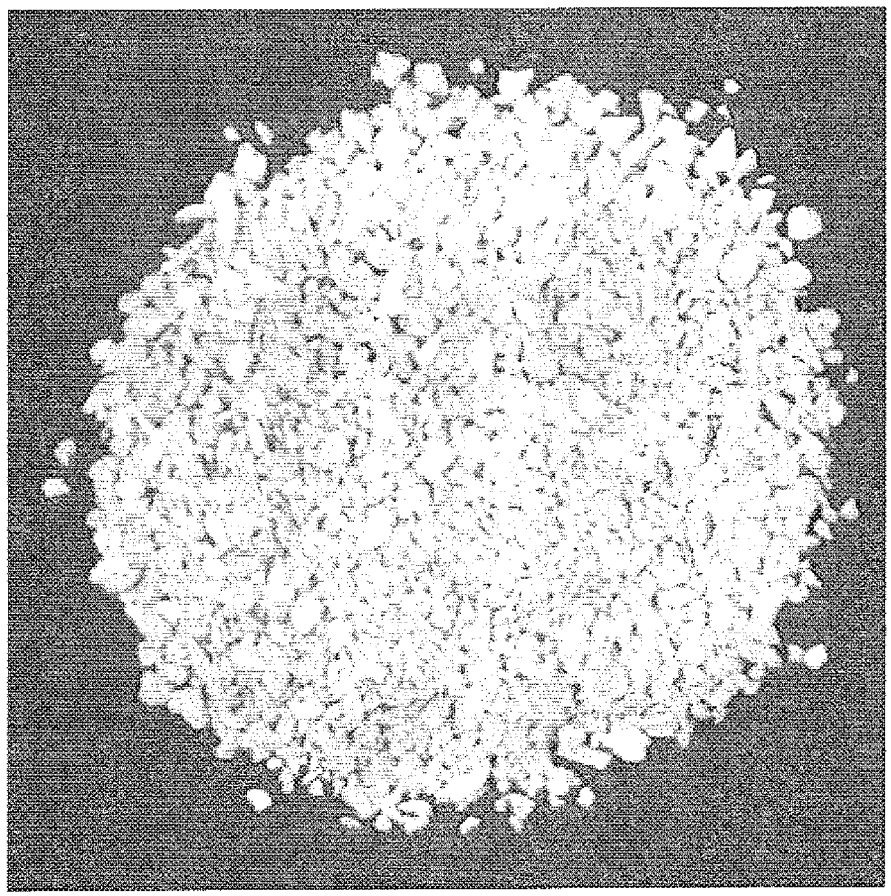
FIGS. 7-9 are photographs of granulated compositions produced in accordance with Example 7.
Figure 8:
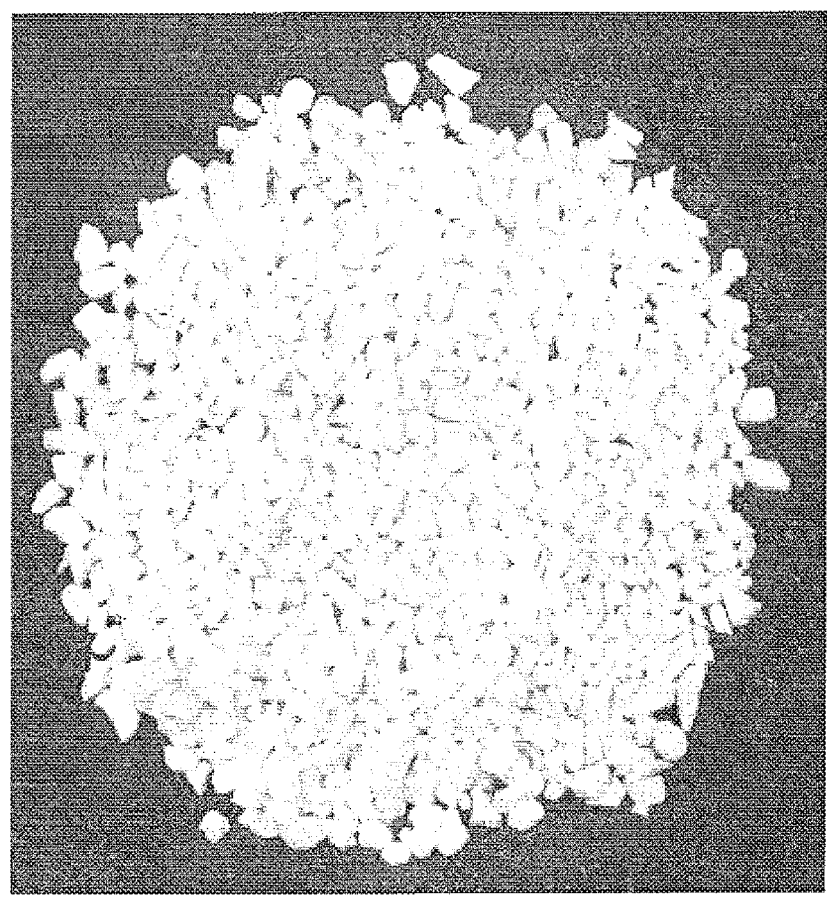
Figure 9:
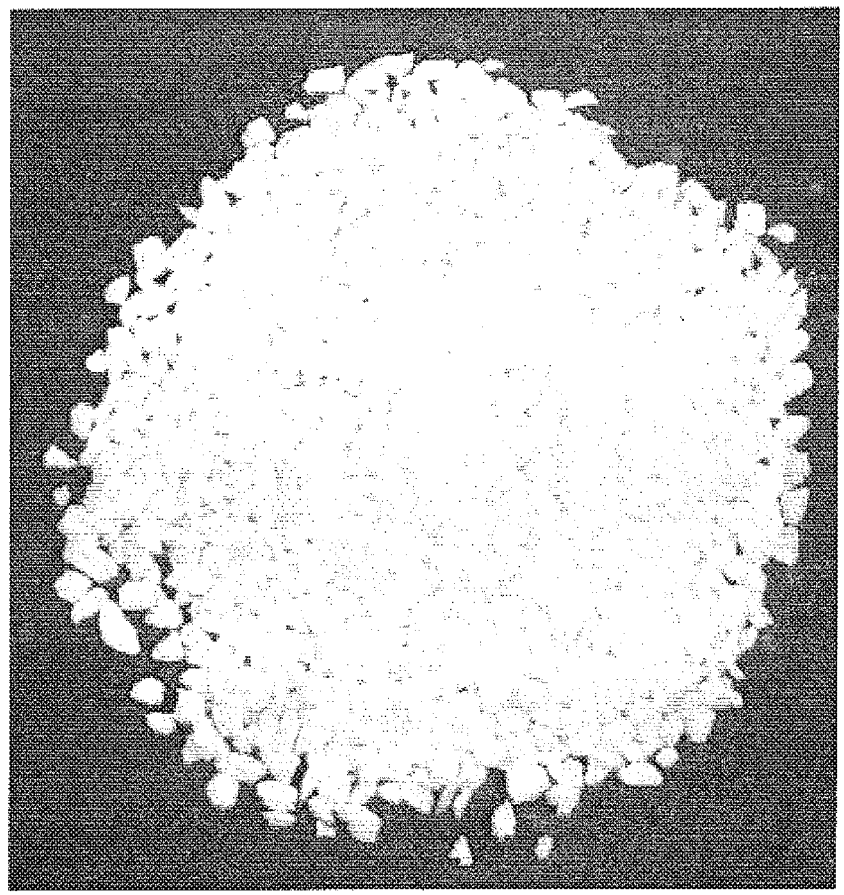

Three granular compositions were made containing PVPP (Polyclar® V, International Specialty Products) with one of two beverage-approved co-ingredients (Table 4). The granules were compacted using a TF Mini Roller Compactor (Vector Corporation, Marion, Iowa) with a screw speed of 40 rpm, a roller speed of 5 rpm, and a roller pressure of 4 tons. The resultant ribbons from the roller compaction process were granulated using an Erweka® AR400 Oscillating Granulator (Heuseristamm, Germany) fitted with a 10 mesh screen. (2 mm). Low-dusting granules were produced. FIGS. 7, 8, and 9 illustrate the granulated products of this Example.

Figure 10:
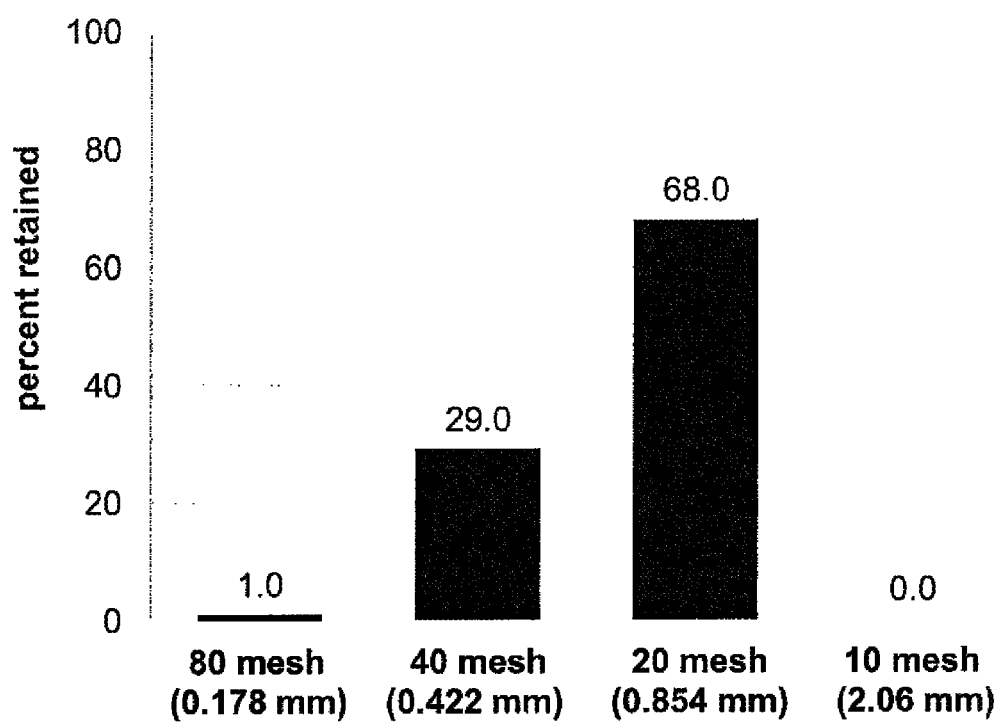
FIGS. 10 and 11 are graphs describing particle size distributions of compositions produced in accordance with Example 7.
Figure 11:
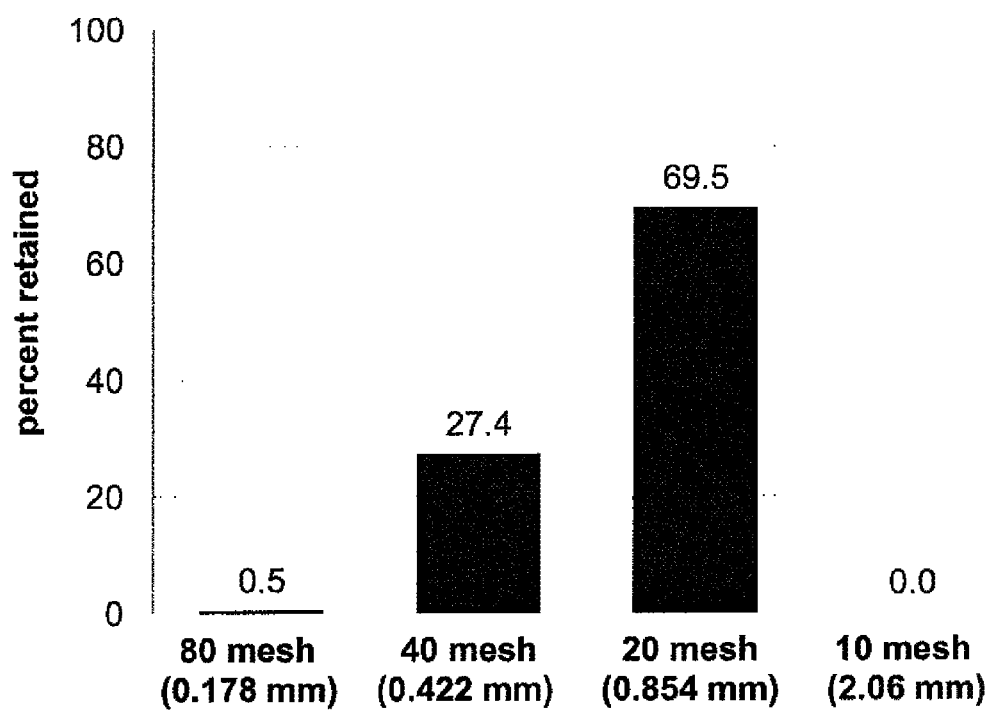

The three granular compositions were size fractionated using four screens, 80 mesh (0.178 min), 40 mesh (0.422 mm), 20 mesh (0.854 mm), and 10 mesh (2.06 mm). As in Example 6, the majority of granulated product was collected on the 20 and 40 mesh screens; no material collected on the 10 mesh screen, and very little product was collected on the 80 mesh screen (Composition A—FIG. 10, Composition B—FIG. 11). In both compositions particles smaller than 80 mesh (178 μm) made up less than 3% of the product.

In a comparison of measurement methods, the particle size distributions of the three granular compositions also were measured using a light-scatter analyzer (LA-950 Particle Size Analyzer, Horiba Ltd.).

TABLE 4

Compositions of formulated PVPP granules

| Compostion | PVPP (Polyclar ® V) | cellulose fiber (Fibra-Cel ® BH-40) | sodium bentonite (Volclay KWK 200) |
|---|---|---|---|
| A | 30% | 15% | 55% |
| B | 70% | 15% | 15% |
| C | 80% | 20% | 0% |

Example 8

Treatment of White Wine for Total Polyphenol Control

Compositions A-C were used to treat a sauvignon blanc white wine and determine the effect of granule composition on total polyphenol content.

First, aqueous slurries of each composition from Example 7 were prepared at 10% (w/v) and hydrated for 24 hours prior to dosing to allow the bentonite component (if present) to gel fully. Samples of the White wine were dosed at room temperature (approximately 22° C.) with each slurry at two dose rates, 25 g/hL and 50 g/hL. Dosed wine samples were given a 1-hour contact time with the granules while under continuous agitation via platform shaker. Afterward, samples were vacuum filtered though a Whatman glass fiber filter. A 5% (w/v) sodium metabisulfite preservative solution was added to all conditions at an addition level of 1.2 ml/L. The one control (processed without any added unprocessed feedstock or composition from Example 7) and three experimental conditions were placed on accelerated testing by incubating them for up to 3 weeks at 50° C.

Filtered aliquots of untreated and treated samples were analyzed by ultraviolet/visible spectroscopy (Cintra® 40, GPC Scientific) and a haze meter, LG Automatic Haze Meter, calibrated using turbidity standards (AMCO Clear Primary Standards, GFS Chemicals). As is standard in the industry, total polyphenol content was the measured absorbance at 275 nm, and samples were diluted with deionized water needed) in order to bring the reading within measurable limits, and the reading was multiplied by dilution faction to give the polyphenol index.

Figure 12:
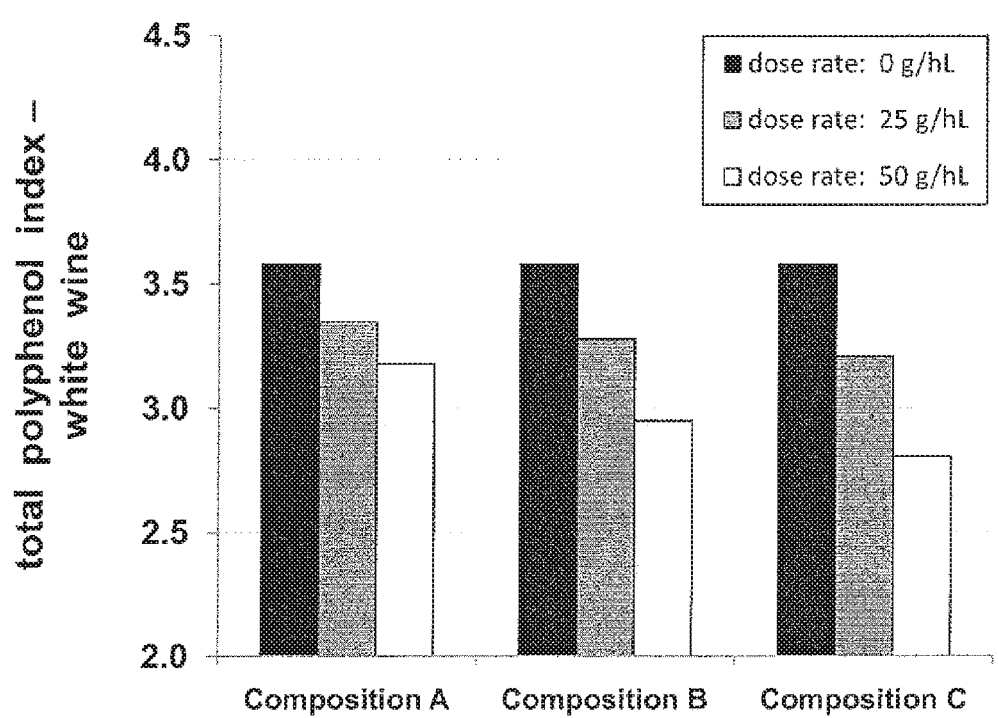
FIG. 12 is a graph of total polyphenol index-white wine for three granular compositions at three dose rates in accordance with Example 8.

Compositions AC provided up to about 1 percentage point reduction (or 28% of the initial) in the total polyphenol content of the white wine (FIG. 12). Consumers may notice this reduction as an improvement in the flavor profile, since the wine is less astringent.

Example 9

Treatment of White Wine for "Pinking"

The method described in Example 8 was repeated in order to determine the effect of compositions A-C (from Example 7) on "pinking" of white wine, being measured as the absorbance at 520 nm.

Figure 13A:
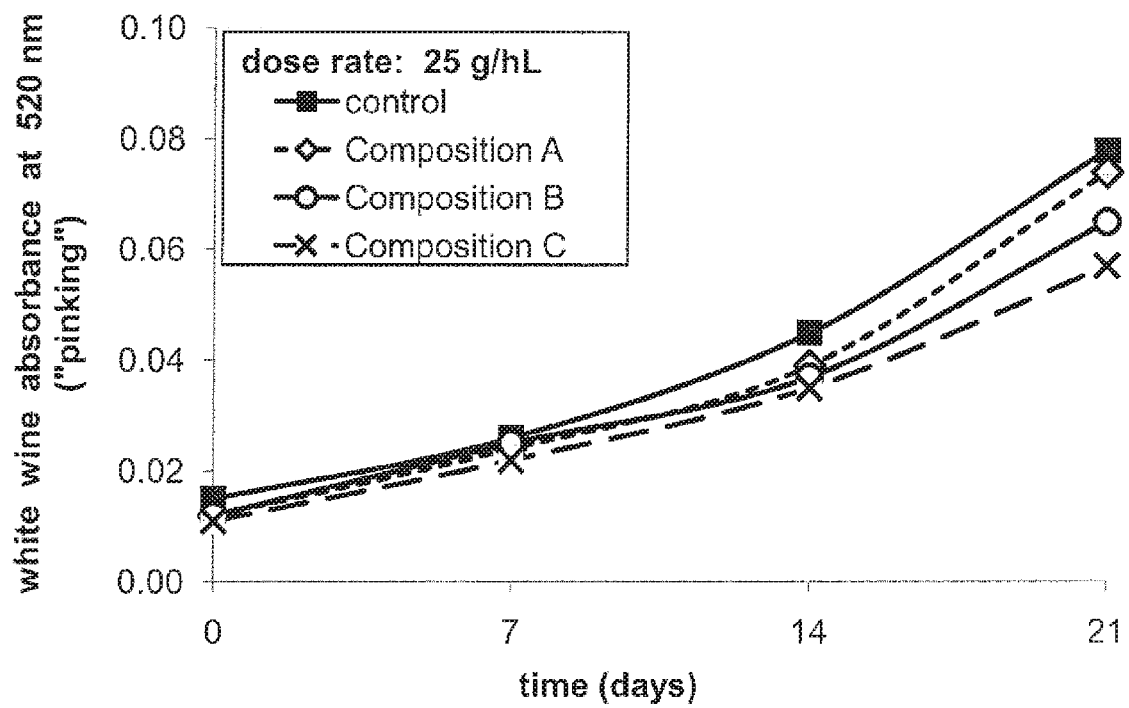
FIGS. 13A and 13B are graphs of white wine absorbance at 520 nm ("pinking") as a function of time for three granular compositions in accordance with Example 9.
Figure 13B:
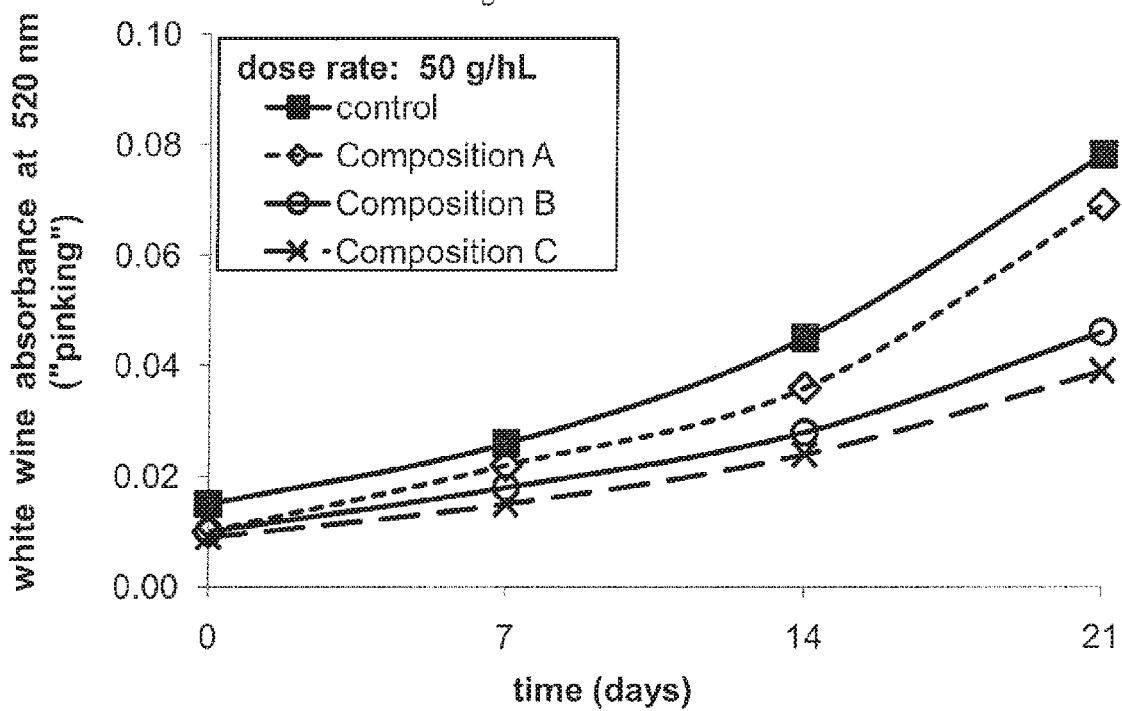

Compositions AC achieved a significant reduction in age-related "pinking" of the white wine. At both dose rates. Compositions A-C lessened the natural increase of "pinking" noted in the untreated control (FIGS. 13A and 13B). The greatest reduction in "pinking" was attained using the treatment of Example 8 and Example 9 at the hither dose rate of 50 g/hL.

Example 10

Treatment of White Wine for "Browning"

The method described in Example 8 was repeated in order to determine the effect of compositions AC (from Example 7) on "browning" of white wine, being measured as the absorbance at 420 nm.

Figure 14A:
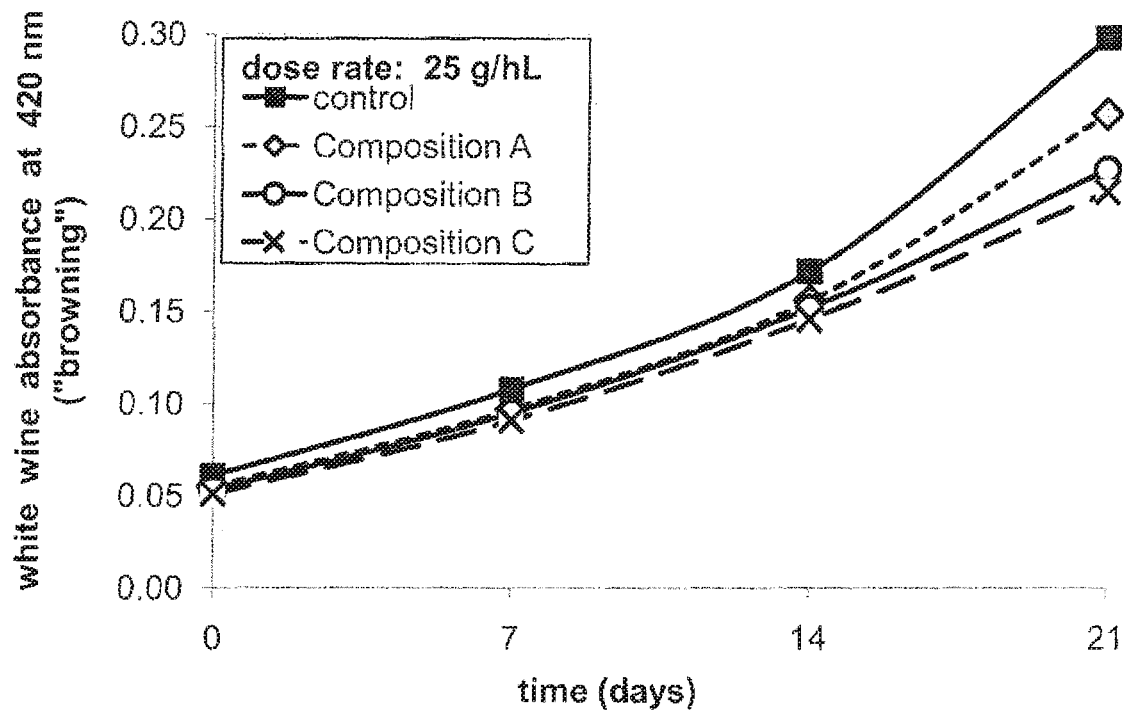
FIGS. 14A and 14B are graphs of white wine absorbance at 420 nm ("browning") as a function of time for three granular compositions in accordance with Example 10.
Figure 14B:
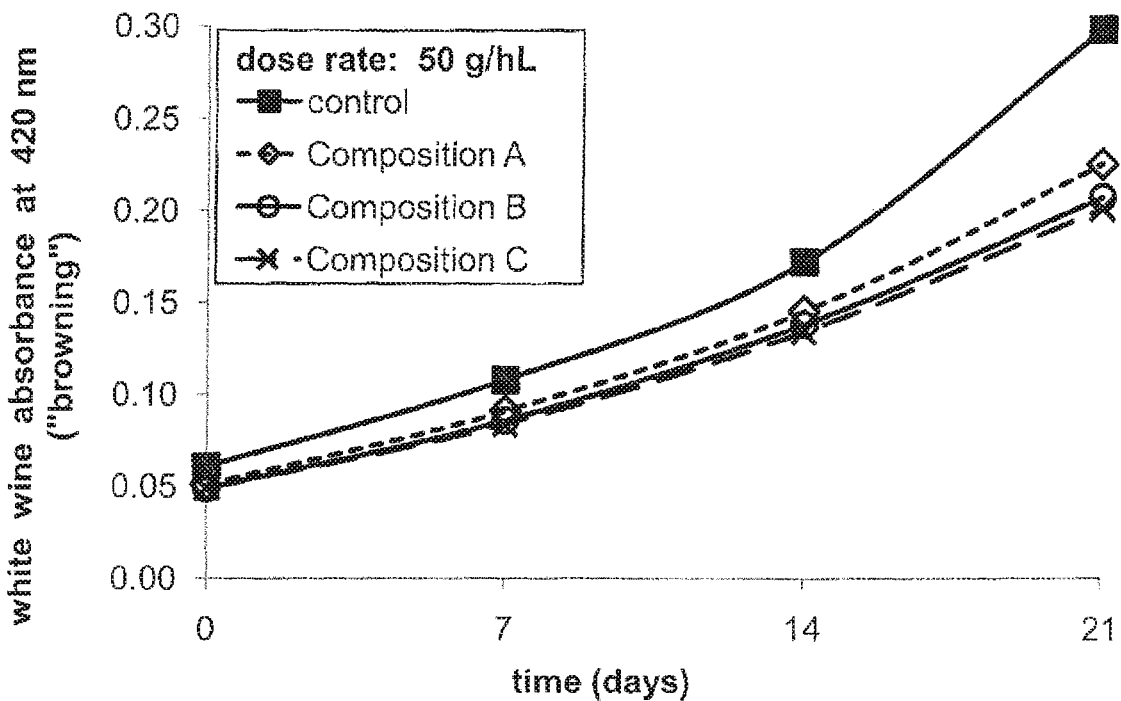

The granulated compositions produced in Example 7 reduced the extent of sauvignon blanc "browning" over time (FIGS. 14A and 14B). Both dose levels of 25 g/hL and 50 g/hL proved effective, with the greater reduction in browning at the higher level.

The "pinking" and "browning" data reveal that the compositions of the invention are useful for treating white wine in order to minimize natural color changes that occur as wine ages. The color agents removed from the white wine also are known by one skilled in the art to contribute to off-flavors. Indeed, it has been experienced that white wine thus treated also exhibit an enhanced flavor profile.

Example 11

Treatment of White Wine for Haze Control

The method described in Example 8 was repeated in order to determine the effect of compositions A-C (from Example 7) on white wine haze, being measured at ambient room temperature (about 22° C.) using an Lg Automatic haze meter calibrated using EBC haze standards.

Figure 15A:
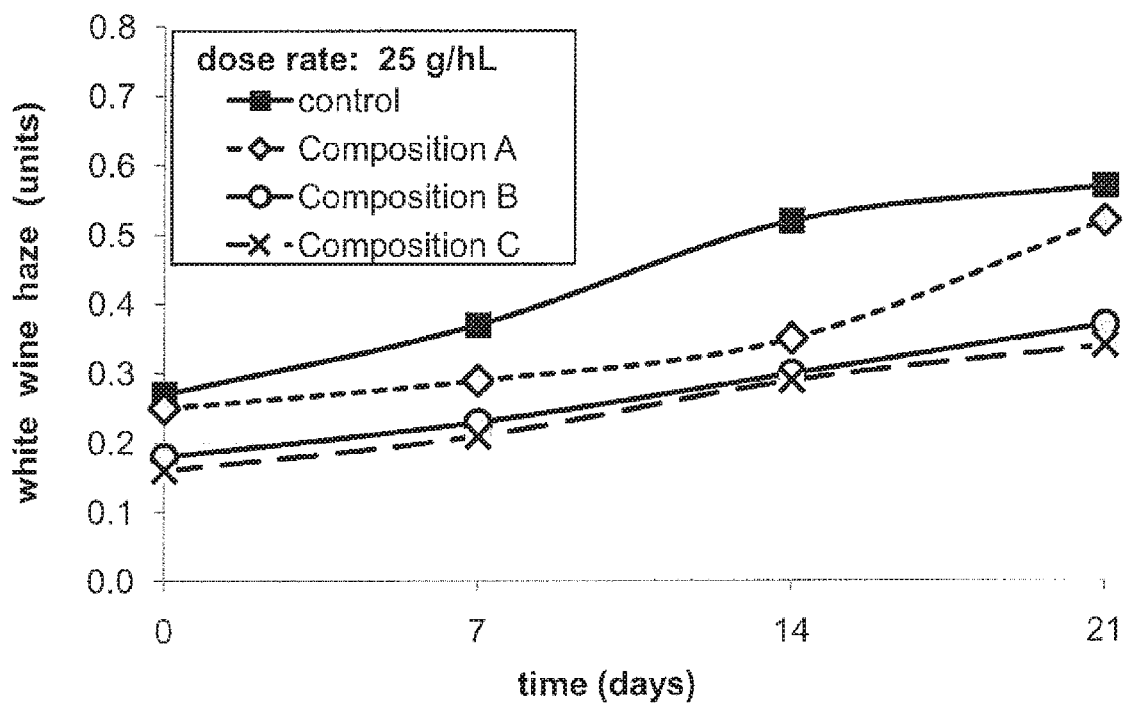
FIGS. 15A and 15B are graphs of white wine haze as a function of time for three granular compositions in accordance with Example 11.
Figure 15B:
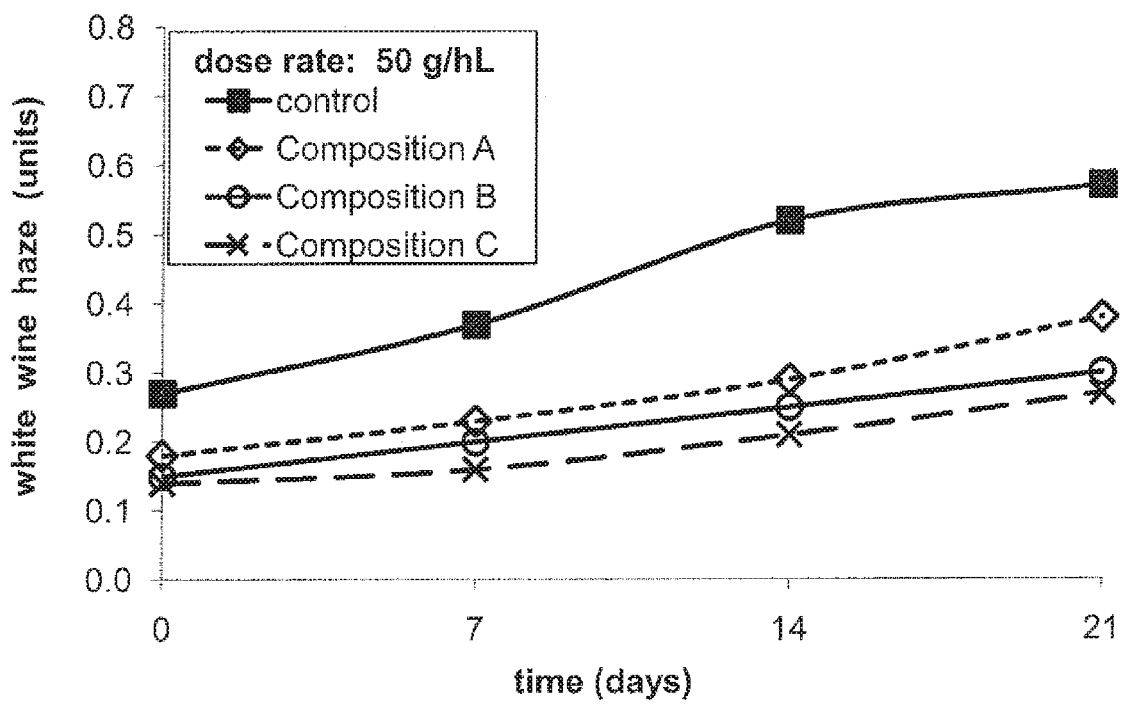

The development of haze considerably decreased after treating white wine with the granulated compositions A-C (FIGS. 15A and 15B). As noted for "pinking" and "browning," compositions B and C controlled the development of haze the best. After 21 days the white wine samples thus treated developed half as much haze as the untreated control.

There is a strong consumed demand for white wines that display little or no haze; clear wines are preferred. Hence, compositions of the invention, and the use thereof to treat white wine find great utility to help wine makers produce a high-value product.

Example 12

Treatment of Red Wine for Total Polyphenol Control

The methods described in Example 8 was repeated to treat a merlot red wine and determine the effect the granulated PVPP compositions on total polyphenol content. The sodium metabisulfite preservative solution level reported in Example 8 was reduced to 0.6 ml/L, and the dose rates also were reduced to 15 g/hL and 25 g/hL.

Figure 16:
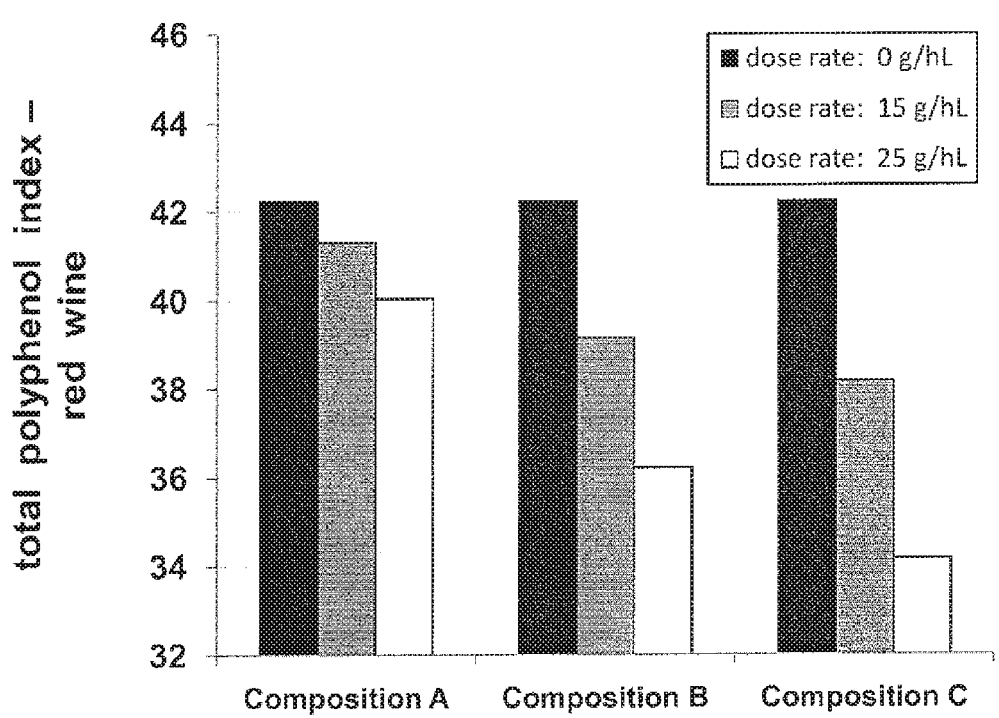
FIG. 16 is a graph of total poly-phenol index-red wine for three granular compositions at three dose rates in accordance with Example 12.

Due in part to the higher level of total polyphenois in red wine than white wine (42 percentage points vs 3.6 percentage points), the blended PVPP granules of Example 7 attained a larger reduction in total polyphenols, up to 8 percentage points (FIG. 16) than was measured for white wine. Both the granule formulation and dose rate were influential in determining the final total polyphenol content of the treated wine. In this experiment, composition C (80% PVPP, 20% cellulose) at 25 g/hL dose rate provided the greatest total polyphenol reduction.

As described in Example 8 for white wine, the reduction in total polyphenols may be noticed as an improvement in the flavor profile, since the wine is less astringent.

Example 13

Treatment of Red Wine for Color Control

The method of Example 10 was repeated wine to assess the influence of PVPP granule formulations on red wine color. Whereas the absorption at 420 nm is used to assess the "browning" of white wine, this value is used to describe the color of red wines. In this example the dose rates were 15 g/hL and 25 g/hL.

Figure 17A:
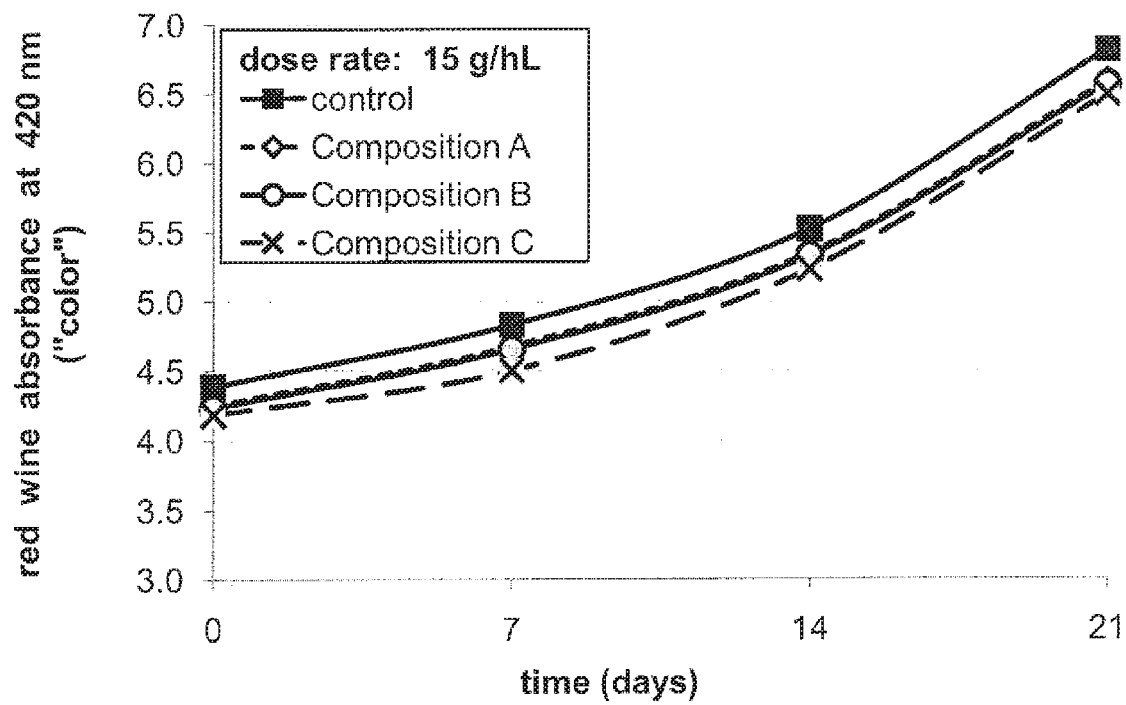
FIGS. 17A and 17B are graphs of red wine absorbance at 420 nm ("color") as a function of time for three granular compositions in accordance with Example 13.
Figure 17B:
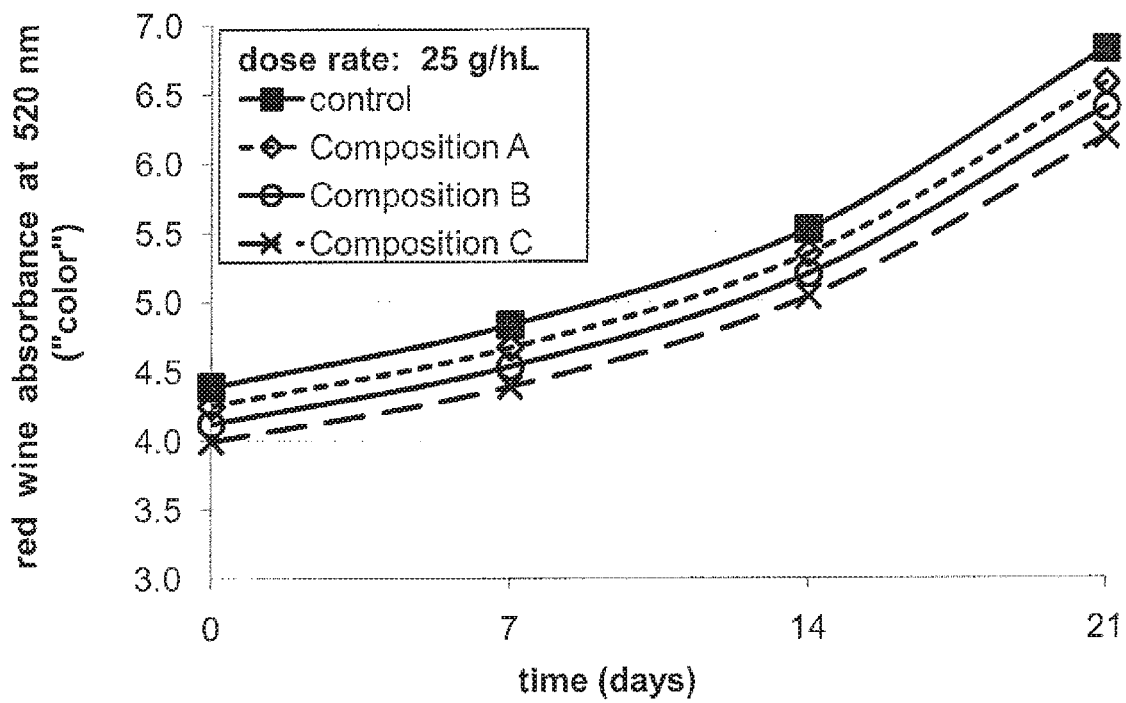

As described for white wine, the formulated granules successfully limited the "color" aging of red wine relative to the untreated control (FIGS. 17A and 17B).

As noted for white wines, there also is a strong consumer demand for red and rose wines that display color brilliance, meaning having a color palate that is rod or pink in nature and without brown. Hence, compositions of the invention, and the use thereof to treat red and rose wines, find great utility to help wine makers produce a high-value product.

The invention has been described in detail with particular reference to preferred embodiments thereof, but it will be understood that variations and modifications can be effected within the spirit and scope of the invention.

What we claim is:

1. A method for the preparation of beverages comprising contacting said beverages with a granular composition comprising at least 15% (w/w) crosslinked polyvinylpyrrolidone (PVPP), an absorbent, and wherein particles 100 μm and smaller make up 10% (w/w) or less of said composition.

2. The method of claim 1 wherein said preparation involves the removal of polyphenol, protein, or both polyphenol and protein.

3. The method of claim 1 wherein said beverage is an alcoholic beverage or a non-alcoholic beverage.

4. The method of claim 3 wherein said alcoholic beverage comprises beer or wine.

5. The method of claim 3 wherein said non-alcoholic beverage comprises fruit juice, tea, or blends thereof.

* * * * *